United States Patent [19]

Tagnon et al.

[11] Patent Number: 4,494,569

[45] Date of Patent: Jan. 22, 1985

[54] APPARATUS FOR CIRCULATING AND REGENERATING A DEGRADABLE SOLUTION SUCH AS A SATURABLE ABSORBER FOR A LASER

[75] Inventors: Luc Tagnon, Saint-Mande; Georges Wajs, Ivry, both of France

[73] Assignee: Essilor International Cie General d'Optique, Creteil, France

[21] Appl. No.: 487,873

[22] Filed: Apr. 22, 1983

[30] Foreign Application Priority Data

Apr. 22, 1982 [FR] France .................. 82 06937

[51] Int. Cl.³ .................................. E03B 7/07
[52] U.S. Cl. .......................... 137/563; 137/93; 137/624.11
[58] Field of Search ............. 137/563, 88, 91, 92, 137/93, 3, 4, 5, 6, 624.11

[56] References Cited

U.S. PATENT DOCUMENTS

| | | | |
|---|---|---|---|
| 2,978,951 | 4/1961 | Christie | 88/14 |
| 3,605,783 | 9/1971 | Pecker et al. | 137/93 |
| 3,746,864 | 7/1973 | Tick et al. | 250/218 |
| 3,815,620 | 6/1974 | Dziomba et al. | 137/88 |
| 4,281,620 | 8/1981 | McChesney et al. | 137/563 |

FOREIGN PATENT DOCUMENTS 2011322  9/1971  Fed. Rep. of Germany .
427128   7/1911  France .

OTHER PUBLICATIONS

H. Brinkschulte et al.–Journal of Physics D, Applied Physics, vol. 7, No. 10, (Letchworth, G.B.j Jul. 1, 1974), pp. 1361–1368, § 2.2. and FIG. 3.

Primary Examiner—Alan Cohan
Assistant Examiner—James R. Shay
Attorney, Agent, or Firm—Charles E. Brown

[57] ABSTRACT

The apparatus comprises a circulation circuit including, in series, a cell containing the degradable solution and a pump for circulating the solution. A second, regeneration circuit is connected to the circulation circuit by valves for injecting into the latter solution having a concentration greater than that of the circulation circuit. The regeneration circuit has a surge tank or a collector vessel for collecting degraded solution from the circulation circuit.

14 Claims, 4 Drawing Figures

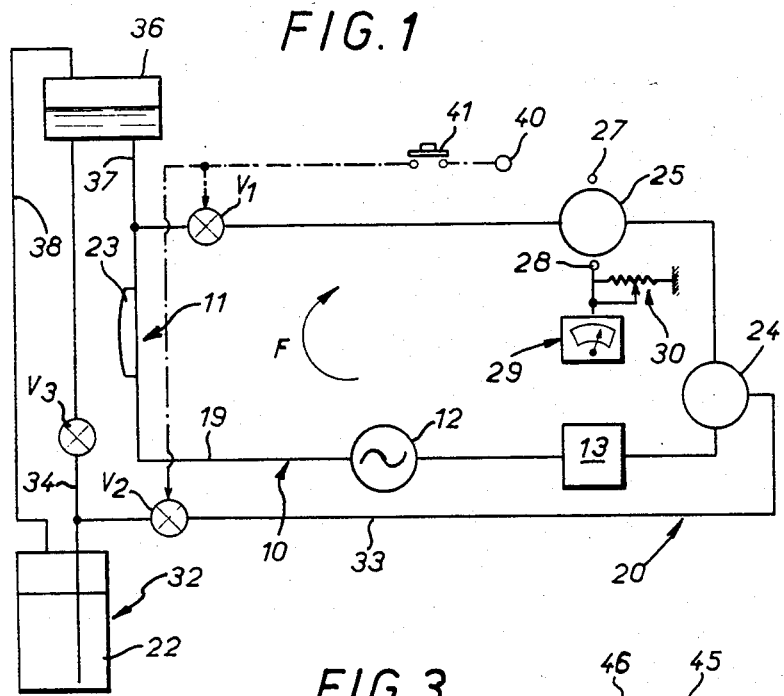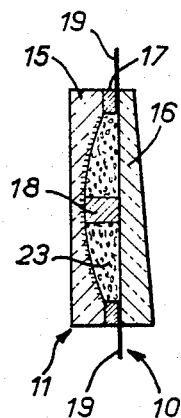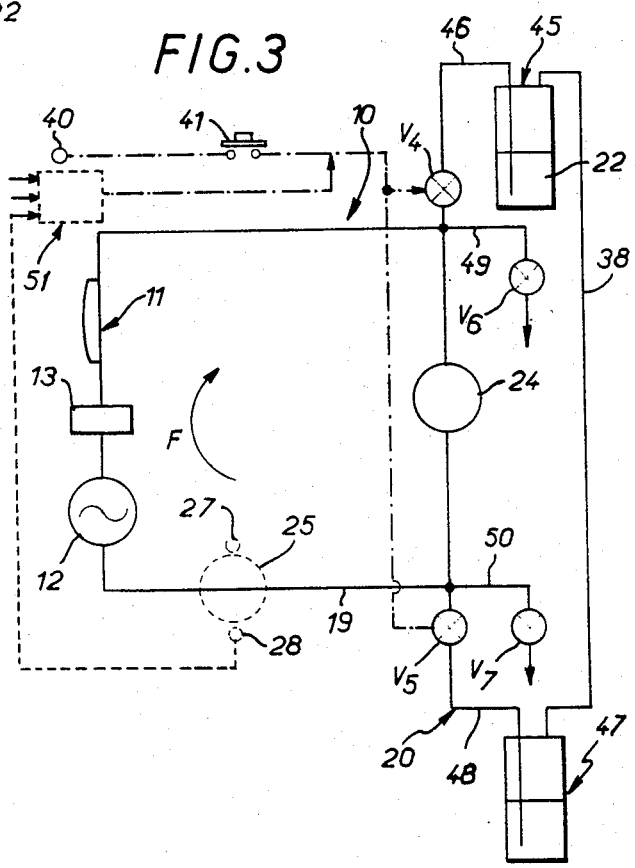

APPARATUS FOR CIRCULATING AND REGENERATING A DEGRADABLE SOLUTION SUCH AS A SATURABLE ABSORBER FOR A LASER

BACKGROUND OF THE INVENTION

The present invention relates generally to the use of a degradable solution of any kind of product, and more particularly through not exclusively, to the use of a saturable absorber in a laser for locked mode operation.

In some applications such as an ophthalmic surgery laser apparatus it is desirable, or even necessary, for the pulses of the laser beam to be extremely short, of the order of a maximum of several tens of picoseconds so that the energy of the light flux transported by the laser beam is sufficient to produce the sought-after effects.

As is known, and without it being necessary to give greater details in this respect in the present application, the laser beam emitted is controlled in a suitable cavity by a control device commonly known as a Q switch which permits emergence of the laser beam only when such very short duration pulses are produced.

By way of example of such a Q switch it is known to use in such a cavity, which is in practice defined by a cell, a solution of a saturable absorber the chemical composition of which is adapted to change abruptly and irreversibly, and therefore also its physical properties, under the effects of such a laser beam.

In practice such a saturable absorber is first opaque to laser radiation and then becomes abruptly transparent, and vice versa. The product sold by Kodak under reference 9740 and commonly referred to as DYE which is used in a chlorobenzene solution has proved to be satisfactory.

Unfortunately, in actual use such a product has been found to be degradable to the extent that under the effects of the light radiation, and particularly the ultraviolet composant thereof, and also the oxygen of the ambiant atmosphere, it gradually loses operating capacity. The operation of the laser equipped with a DYE cell uncontrollably changes from the locked mode to the Q switching mode which is detrimental to the sought-after results in at least some fields of use.

To at least partially overcome this drawback, and taking into account the fact that in practice only a small area of the DYE cell, herein referred to as the active zone, is in fact affected by the laser beam, it has already been proposed to put such a DYE cell in a circulating circuit having a series connected pump for pumping the solution and thereby continuously changing the part of the solution present in active zone of the cell.

But when all the solution in the circulation system has degraded below a threshold level the entire solution must be changed. This is a relatively time-consuming and delicate operation during which period the laser apparatus may not be used and if special monitoring means are not employed the solution may not be changed as soon as actually necessary.

It is also known in U.S. Pat. No. 2,978,951 and French Pat. No. 427,128, which deal with a solution of one of more conventional dyes and not with a degradable solution within the meaning of the present invention, to connect to a circuit using such a solution or a circuit for circulating the solution, at least one tank containing at least one dye constituent a predetermined amount of which is injected, at will, under the control of valves, into the circuit to readjust the solution.

Such a readjustment of the dye solution is not necessarily suitable for degradable solutions of the type concerned by the present invention, namely in case all the resulting products of degradation cannot be allowed to remain in the solution in the circulation circuit without causing operating problems and/or in case the circulation circuit contains a fixed amount of solution.

SUMMARY OF THE INVENTION

A general object of the present invention is the provision of an apparatus which enables the above drawback to be overcome and at the same time provides other advantages.

According to the invention there is provided an apparatus using some sort of degradable solution such as a saturable absorber for a laser. The apparatus is of the type comprising a first circulation circuit in which is provided, in series, a cell for containing the solution and a pump for delivering the solution. The apparatus also comprises a second circuit and flow control means for controllably injecting into the circulation circuit fresh solution having a concentration greater than that of the solution in use. The second circuit comprises a main tank for containing fresh, concentrated solution and is adapted to be connected to the circulation circuit by the flow control means. The improvement comprises an auxiliary tank in second circuit forming a sump tank or collector vessel which is itself connected to the circulation circuit.

It is thus advantageously possible, whenever necessary, to introduce into the circulation circuit an additional supply of atoms of fresh, nondegraded saturable absorber and thereby maintain the solution in use in the circulation at a satisfactory concentration for such a saturable absorber to prolong the service life of the solution before it has to be completely changed while at the same time removing from the circulation circuit into the auxiliary tank an amount of the solution in use sufficient for prolonging the service life of the solution in use in the circulation circuit.

From this point of view the circuit comprising such an auxiliary tank thus forms a regeneration circuit for regenerating the degradable solution.

Preferably, a buffer tank forming a mixing chamber is provided in the circulation circuit and has a volume greater than that of the rest of the circulation circuit, for example at least twice that of the circulation circuit. Such a buffer tank permits the mixing of the solution in use in the circulation circuit and the fresh solution injected by the regeneration circuit into the circulation circuit in an acceptably short period of time substantially less than, for example, half an hour.

Preferably, according to an additional feature of the invention a spectrophotometer is provided in the circulation circuit for monitoring the solution in use in the circulation circuit.

It has been established that with such a saturable absorber solution the spectroscopic analysis of the solution advantageously permits a one-to-one determination of its rate of degradation and thereby the capacity or effectiveness with regard to the sought after results.

As a function of observations made with a spectrophotometer the flow control means for the regeneration circuit may be controlled manually. It may also be controlled automatically by means of a microprocess control unit.

The present invention advantageously lends itself to various embodiments in respect to both the flow control means and the regeneration circuit.

Further, in any event, owing to the auxiliary tank the filling of the circulation circuit of the apparatus for startup, as well as changes of the solution in the main tank, is facilitated.

These and other features and advantages of the invention will become apparent from the description which follows, given by way of example, with reference to the accompanying diagrammatic drawings.

BRIEF DESCRIPTION OF THE DRAWINGS

FIG. 1 is a circuit diagram of the apparatus embodying the present invention;

FIG. 2 is a larger scale axial sectional view of a cell of the apparatus; and

FIG. 3 is a view similar to FIG. 1 for another embodiment of the invention; and

DESCRIPTION OF THE PREFERRED EMBODIMENTS

Figure 4:
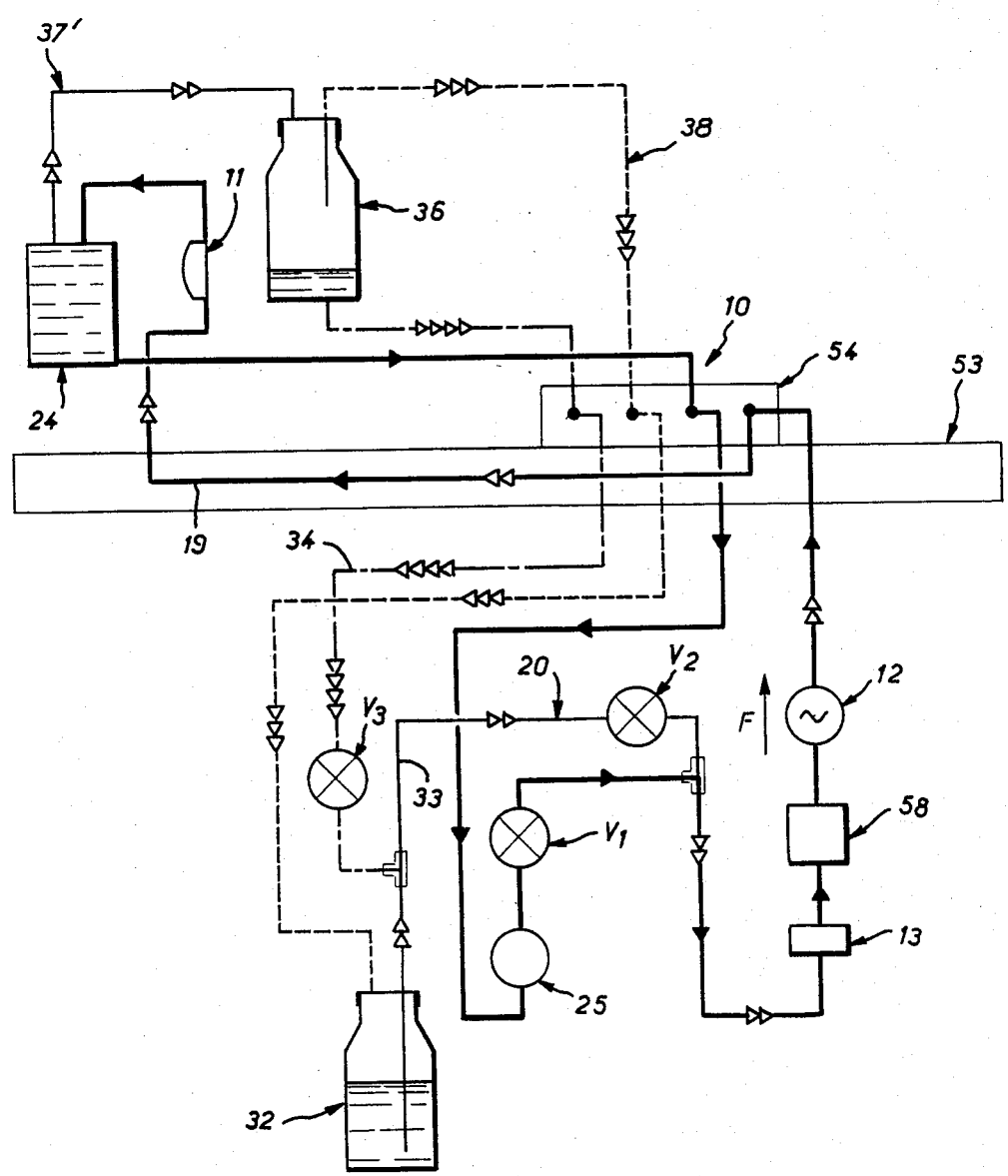
FIG. 4 is another view similar to that of FIG. 1 for a practical embodiment having the same mode of operation as that of FIG. 1.

As illustrated in the drawings the apparatus embodying the invention which is adapted to use any sort of degradable solution in any kind of equipment, and more particularly for the use of a saturable absorber in a laser apparatus is of the type comprising a first, circulation circuit 10 including, in series, a cell 11 containing the solution, a pump 12 for pumping the solution, and a filter 13 for holding back solid debris or other foreign bodies which may be present in the solution, particularly precipitates.

In case a saturable absorber for a laser of the type mentioned above is used in the circulation circuit, the cell 11 forms, as shown in FIG. 2, a cavity for using such a solution in a laser. The cell 11 comprises a concave mirror 15 which defines the back of the cavity and a window 16 with a slightly inclined inlet face which closes the front of the cavity in cooperation with a peripheral gasket 17. In practice only the central part 18 of the cavity formed by the cell 11 is in direct contact with the laser beam. In FIG. 2 the central part 18 is represented by hatching.

The associated pump 12 may be of any type and the filter 13 may be of any type, for example, it may be made of sintered glass.

The various components of the circulation circuit 10 are connected to one another in a closed loop by the successive sections of the line 19 defining the circulation circuit 10.

The apparatus according to the invention further comprises a second, regeneration circuit 20 connected at some point along the circulation circuit 10 for injecting fresh, concentrated solution 22 into the circulation circuit under the control of flow control means, the fresh solution 22 having a concentration greater than that of the solution 23 in use in the circulation circuit. Preferably, the concentration of the fresh solution 22 is several times greater than that of the solution 23 in use, for example five times greater, which is presumed to be sufficient to satisfy the sought-after results.

In the FIG. 1 embodiment a buffer tank 24 forming a mixing chamber is connected to the circulation circuit 10 and the buffer tank 24 interconnects the regeneration circuit 20 and the circulation circuit 10. Preferably, the buffer tank 24 has a volume greater than that of the rest of the circulation circuit 10, for example, a volume at least twice that of the rest of the circulation circuit.

The buffer tank 24 is upstream of pump 12 relative to the direction F of the flow of solution 23 in the circulation circuit 10 and therefore on the admission side of pump 12. The cell 11 is downstream and therefore on the delivery side of pump 12.

In the FIG. 1 embodiment a spectrophotometer 25 is connected in the circulation circuit 10 for monitoring the solution 23 in use in the circulation circuit. Such a spectrophotometer 25 may be of any known construction and need not be described in detail herein. However, as diagrammatically shown the spectrophotometer 25 in FIG. 1 comprises a pilot light source 27 for operating the spectrophotometer and a photocell 28 for collecting the light radiation from the light source 27 traversing the spectrophotometer. For example, as illustrated, the voltage output of the photocell 28 may be measured by a voltmeter 29 having an input potentiometer 30 for adjusting the reading. By properly adjusting the potentiometer 30 when the concentration of the solution 23 circulating in the circulation circuit 10 has a sufficient value for the sought-after results, the needle of the voltmeter 29, as shown in FIG. 1, is in a predetermined range. To adjust the device a suitable calibration may be carried out with a light meter.

As is known per se the regeneration circuit 20 of the present invention comprises a first or main tank 32 for fresh, concentrated solution 22 controlled by associated flow control means and connected by a line 33 to the circulation circuit 10. In the illustrated embodiment of FIG. 1, the main tank 32 is connected to the circulation circuit 10 upstream of the admission side of the pump 12 and in practice the line 33 is connected to the buffer tank 24.

According to the invention the regeneration circuit 20 comprises a second or auxiliary tank 36 which is connected by a line 37 to the circulation circuit 10. In the embodiment of FIG. 1, the auxiliary tank 36 is connected to the circulation circuit 10 downstream of the delivery side of pump 12 and, in practice, downstream of the cell 11.

Further, in this embodiment the main tank 32 is disposed in the lower part of the device and is connected to the auxiliary tank 36 through a line 34 which forms a T-coupling with the line 33 and the auxiliary tank disposed in the upper part of the apparatus forms a sump tank or collector vessel.

In practice a line 38 connects the top of the interior of the main tank 32 to the headspace of the auxiliary tank 36. Preferably, a neutral gas with respect to the solution, e.g. neon, makes up the atmosphere in the headspace in each of the tanks 32, 36.

Preferably, the main tank 32, and only the main tank in the present embodiment, in interchangeable. It therefore has couplings for detachable connection to the associated lines and more particularly, to line 33 and its branch line 34 and line 38.

In any event, the main tank 32 is preferably opaque to the radiation to protect the fresh solution 22 contained therein from radiation.

In the embodiment of FIG. 1, the associated flow control means comprises a first valve $V_1$ which is disposed in the circulation circuit 10 downstream of the connection with line 37, a valve $V_2$ interposed in line 33 downstream of the connection with line 34 and a valve $V_3$ interposed in line 34. Valves $V_1$, $V_2$, $V_3$ may all be manually operable. But at least one of valves $V_1$, $V_2$, $V_3$ may be a solenoid valve. For example, as diagrammatically illustrated in FIG. 1, only valve $V_3$ is a manual valve; valves $V_1$, $V_2$ are solenoid valves adapted to be supplied by some appropriate current source 40 controlled by a push button switch 41 adapted to be actuated by the operator.

In any event, each of valves $V_1$, $V_2$, $V_3$ may, as is known per se, have one of two positions, open O and closed C.

They advantageously permit the following operations to be carried out:

(A) filling
(B) end of filling
(C) circulating the solution in use in the circulation circuit 10
(D) injecting fresh solution into the circulation circuit 10
(E) draining the entire apparatus according to the following truth table of their respective states:

|       | A | B | C | D | E | F |
|-------|---|---|---|---|---|---|
| $V_1$ | O | O | O | C | C | O |
| $V_2$ | O | C | C | O | C | O |
| $V_3$ | C | C | C | C | O | O |

The circulation circuit 10 is filled with valves $V_1$ and $V_2$ open and valve $V_3$ closed, introducing a solution of predetermined concentration corresponding to the desired results. During filling, the solution flows into the circulation circuit 10 and at least partly fills the auxiliary tank 36.

Since the auxiliary tank 36 is located at the top of the apparatus the circulation circuit 10 is completely filled, and any degassing will also involve the auxiliary tank 39 as well.

Once the apparatus has been filled with the starting solution, the pump 12 may be turned on for pumping the solution 23 in the circulation circuit 10. The operator monitors, from time to time or continuously, the concentration of the solution 23 by means of voltmeter 29 to ensure that the concentration remains within acceptable limits.

When the concentration of solution 23 reaches its lower limit the operator presses pushbutton 41 to change the positions of valves $V_1$ and $V_2$ to operate the regeneration circuit 20. After waiting for the period necessary for mixing the fresh, concentrated solution 22 injected into the circulation circuit 10 with the solution 23, the new concentration of the solution 23 is checked by reading the voltmeter 29. Therafter the operator has to press pushbutton 41 each time it is necessary to bring the concentration of the solution 23 in the circulation circuit back to an acceptable level for the desired results.

Alternatively, the apparatus may be calibrated to permit the operator to keep the pushbutton depressed for a given period in order to renegerate the solution in the circulation circuit to the desired level of concentration.

As the fresh solution 22 is injected into the circulation circuit 10 the solution 23 in use in the circulation circuit is carried toward the auxiliary tank 36 and returned to the main tank 32 via line 38 for the gas atmosphere.

Once the fresh, concentrated solution 22 has been depleted the main tank 32 is drained through valve $V_3$. Thereafter the opening of valves $V_1$ and $V_2$ permits the entire circulation circuit 10 to be emptied.

Thereafter the main tank 32 is replaced by another full main tank 32 containing fresh concentrated solution 22.

The foregoing steps may then be repeated.

It will have been noted that only a single tank, namely main tank 32, has to be handled. It should also be noted that it is possible to scavenge the circulation circuit 10 with the neutral gas to eliminate any oxygen therein before refilling the circulation circuit 10. Finally, it will be noted that the apparatus according to the invention including the circulation circuit 10 and the regeneration circuit 20 is entirely hermetically sealed and therefore it may be held under neutral atmosphere which helps prolong the service life of solution in use in the circulation circuit 10. If desired the neutral atmosphere may be pressurized.

In the embodiment of FIG. 3, the regeneration circuit 20 comprises at the top a first or main tank 45 for fresh, concentrated solution 22 controlled by associated flow control means and connected to the circulation circuit 10 to permit gravity flow of its contents thereinto. A line 46 with a syphon is provided for this purpose. At the bottom of the apparatus is a second or auxiliary tank 47 comprising a collector vessel which is controlled by the flow control means to connect it with the circulation circuit 10 to collect by gravity all or part of the contents of the circulation circuit.

In practice, in the illustrated embodiment line 46 is connected to the circulation circuit 10 upstream of the buffer tank 24 and line 48 is connected to the circulation circuit 10 downstream of the buffer tank 24. In addition, lines 49 and 50 are together provided for emptying the circulation circuit 10.

As above, line 38 connects the headspaces of tanks 45 and 47 for communication of the neutral atmosphere contained in the headspaces to each other.

Finally, in the FIG. 3 embodiment the flow control means comprises a valve $V_4$ mounted along line 46 and a valve $V_5$ mounted along return line 48, valve $V_6$ being provided on the line 49 and valve $V_7$ being provided on the line 50.

As above, valves $V_4$ and $V_5$ may be simply controlled manually or as diagrammatically illustrated in chain-dotted lines in FIG. 3, comprise solenoid valves actuated by a pushbutton 41 operated by the operator.

Also as above, and diagrammatically represented in dotted lines in FIG. 3, a spectrophotometer 25 may be provided.

According to a further feature which may be incorporated in the FIG. 1 embodiment as well, the flow control means controlling the starting of the regeneration circuit 20 may be automatically controlled instead of manually controlled as above. A microprocessor control unit 51, schematically represented in dotted lines in FIG. 3 for controlling the operation of the regeneration circuit 20, receives the output voltage from photocell 28 associated with the spectrophotometer 25 and, among other things, controls the operation of the flow control means. The detailed construction of such an automatic control means is matter for those ordinarily skilled in the art and will not be described here.

The embodiment illustrated in FIG. 4 is of the same type illustrated in FIG. 3. The main tank 32 is at the bottom of the apparatus and the auxiliary tank 36 forming a sump tank or collector vessel is at the top. Like parts will be designated by same references.

Above and below a horizontal support 53 are mounted the parts of the apparatus according to the invention, and at 54 an angle member mounted on the horizontal support 53 couples at least some of the lines of the apparatus between the upper and lower parts.

Line 19 common to the circulation circuit 10 and the regeneration circuit 20 runs along at least part of the length of the horizontal table 53 and preferably has a thermostat for controlling the temperature of the solutions.

In FIG. 4 the circulation circuit 10 is shown in solid lines with simple arrowheads indicating the direction of flow therein and the regeneration circuit 20 is also shown in solid lines with double arrowheads indicating the direction of flow therein. Also in FIG. 4 is an overflow circuit shown by dotted lines with triple arrowheads indicating the direction of flow therein comprising a line 38 connecting the atmosphere in headspace above the solution level in the auxiliary tank 38 and the main tank 36. Also an auxiliary tank draining circuit is shown in chain-dotted lines, with quadruple arrowheads indicating the direction of flow therein, comprising line 34 controlled by valve $V_3$.

In this practical embodiment the buffer tank 24 is disposed on the delivery side of the pump 12 downstream of cell 11 which favors filling of the buffer tank 24 with the possibility of venting air present at that level. Consequently the connection between the main tank 32 and the circulation circuit 10 is not via buffer tank 24, the corresponding line 33 simply forming a T-connection with line 19 of the circulation circuit 10.

In conjunction therewith the connection of the auxiliary tank 36 with the circulation circuit 10 is via buffer tank 24, a line 37' being provided for this purpose between the buffer tank 24 and the auxiliary tank 36 in place of line 37.

Finally in the FIG. 4 practical embodiment the relative positions of valve $V_1$ and the spectrophotometer 25 with respect to the direction of the flow of the solution in use in the circulation circuit are reversed. Between the filter 13 at the admission side of pump 12 and the latter is provided a conventional flow rate measuring device 58.

I1 all other respects this embodiment is identical to that of the FIG. 3 embodiment.

Its operation is similar too. The filling of the circulation circuit is effected by closing valves $V_1$ and $V_3$ and opening valve $V_2$. The fresh, concentrated solution drawn by pump 12 from main tank 32 is delivered to the buffer tank 24 and when the latter is full it fills the auxiliary tank 36.

Valve $V_2$ is then closed and while valve $V_3$ remains closed and pump 12 operates, valve $V_1$ is open so that any air which may be present in line 19 between buffer tank 24 and valve $V_1$ is vented.

The corresponding truth table is as follows:

|  | A | B |
|---|---|---|
| $V_1$ | C | O |
| $V_2$ | O | C |
| $V_3$ | C | C |

After the fresh, concentrated solution flows several times through the circulation circuit 10 the air which was still in the lines is collected at the top of the buffer tank 24. It is then vented and once again after filling, according to the foregoing procedure.

The apparatus is then ready to be used in accordance with the columns C and D of the first truth table. When the auxiliary tank 36 is full it may be emptied in accordance with column E of the first truth table by recovering the used solution which flows out of the line 33 downstream of valve $V_3$.

But in the course of operation the auxiliary tank may become full, in which case the used solution contained therein is delivered to the main tank 32 via line 38 which then functions as an overflow tank.

Thereupon, despite the operation of the regeneration circuit the concentration of the solution in the circulation circuit monitored by the spectrophotometer 25 does not increase and the apparatus must then be entirely emptied.

First, to empty the buffer tank 24 and the spectrophotometer 25, cell 11 is disconnected from the buffer tank 24 and after closing off sections thus isolated, valves $V_1$ and $V_2$ are opened while valve $V_3$ is left closed. A neutral gas is then let in, e.g. via line 38, to scavenge the apparatus.

In a second period the cell 11 is again connected to buffer tank 24, valves $V_1$ and $V_3$ being closed and valve $V_2$ being open, the cell 11, the pump 12, the flow rate measuring means 58 and the filter 13 are all emptied before once again scavenging the apparatus with the neutral gas.

The corresponding truth table is as follows:

|  | $F_1$ | $F_2$ |
|---|---|---|
| $V_1$ | O | C |
| $V_2$ | O | O |
| $V_3$ | C | C |

In a third period the auxiliary tank 36 is emptied according to column E of the first truth table.

Obviously the present invention admits of various alternatives and modifications and combinations of the parts of the foregoing embodiments without departing from the spirit and scope of the invention.

What is claimed is:

1. Apparatus for circulating and regenerating a degradable solution such as a saturable absorber for a laser, said apparatus comprising a first, circulation circuit including, in series, a cell adapted to contain the solution, a pump for pumping the solution and a second regeneration circuit carrying fresh, concentrated solution, flow control means for injecting said fresh concentrated solution into said circulation circuit, said second, regeneration circuit comprising a main tank for containing said fresh concentrated solution and an auxiliary tank defining a sump tank or collector vessel for collecting degraded solution from said circulation circuit.

2. Apparatus according to claim 1, wherein said main tank is connected to said circulation circuit upstream of the admission side of said pump and said auxiliary tank is located downstream of the delivery side of said pump, relative to the direction of flow of solution therein.

3. Apparatus according to claim 1, wherein said main tank is disposed in the lower part of said apparatus and said auxiliary tank is located in the upper part of said apparatus.

4. Apparatus according to claim 1, wherein main tank is also connected to auxiliary tank, said flow control means control the flow of solution between said main tank and said auxiliary tank.

5. Apparatus according to claim 1, wherein said main tank is disposed in the upper part of said apparatus so that its contents can flow out under the force of gravity, said auxiliary tank in the lower part of said apparatus collecting the contents thereof under the action of gravity.

6. Apparatus according to claim 1, wherein a line connects the headspaces in said main and auxiliary tanks.

7. Apparatus according to claim 1, wherein a buffer tank is connected in said circulation circuit and defines a mixing chamber having a volume greater than that of the rest of said circulation circuit.

8. Apparatus according to claim 7, wherein the volume of said mixing chamber is at least twice the volume of the rest of said circulation circuit.

9. Apparatus according to claim 1, wherein said main tank is disposed in the lower part of said apparatus and said auxiliary tank disposed in the upper part of said apparatus, a buffer tank defining a mixing chamber being connected in said circulation circuit having a volume greater than that of the rest of said circulation circuit.

10. Apparatus according to claim 9, wherein the volume of said mixing chamber is at least twice the volume of the rest of said circulation circuit.

11. Apparatus according to claim 9, wherein said buffer tank connects said regeneration circuit to said circulation circuit, said flow control means controlling the flow of solution between said main tank and said buffer tank.

12. Apparatus according to claim 9, wherein said buffer tank connects said auxiliary tank to said circulation circuit.

13. Apparatus according to claim 9, wherein said buffer tank is disposed to the discharge side of said pump, downstream of said cell relative to the direction of flow of solution in said circulation circuit.

14. Apparatus according to claim 1, wherein a spectrophotometer is disposed in said circulation circuit for monitoring the solution in use therein.

* * * * *